US006608310B2

(12) United States Patent
Soluri et al.

(10) Patent No.: US 6,608,310 B2
(45) Date of Patent: Aug. 19, 2003

(54) MODULAR HIGH SPATIAL RESOLUTION SCINTIGRAPHIC DEVICE WITH MULTIPLE INDEPENDENT PHOTOMULTIPLIERS AND WITH EXTENSIBLE VISUALISATION AREA

(75) Inventors: Alessandro Soluri, Rome (IT); Raffaele Scafe', Anguillara S. (IT); Nunzio Burgio, Rome (IT); Alfiero Schiaratura, Rome (IT)

(73) Assignee: C.N.R. - Consiglio Nazionale Delle Ricerche, Rome (IT)

( * ) Notice: Subject to any disclaimer, the term of this patent is extended or adjusted under 35 U.S.C. 154(b) by 195 days.

(21) Appl. No.: 09/924,096

(22) Filed: Aug. 8, 2001

(65) Prior Publication Data

US 2002/0175290 A1 Nov. 28, 2002

(30) Foreign Application Priority Data

May 23, 2001 (IT) .................................... RM2001A0028

(51) Int. Cl.$^7$ ............................................... G01T 1/164
(52) U.S. Cl. .................... 250/366; 250/361 R; 250/369
(58) Field of Search ....................... 250/361 R, 363.01, 250/366, 369

(56) References Cited

U.S. PATENT DOCUMENTS

| | | |
|---|---|---|
| 5,252,830 A | 10/1993 | Weinberg |
| 5,323,006 A | 6/1994 | Thompson et al. |
| 5,519,221 A | 5/1996 | Weinberg |
| 5,783,829 A | 7/1998 | Sealock et al. |
| 5,864,141 A | 1/1999 | Majewski et al. |
| 6,021,341 A | 2/2000 | Scibilia et al. |
| 6,232,605 B1 | 5/2001 | Soluri et al. |
| 6,242,744 B1 | 6/2001 | Soluri et al. |
| 6,455,856 B1 * | 9/2002 | Gagnon ....................... 250/366 |

FOREIGN PATENT DOCUMENTS

WO    WO 96/37791 A1    11/1996

OTHER PUBLICATIONS

Scafe Raffaele and Tati Angelo, "Simulation of the response of scintillation imaging devices based on crystal matrices coupled to position–sensitive light multipliers", Scintillation Image Simulator, Mar. 7, 2001.

* cited by examiner

*Primary Examiner*—Constantine Hannaher
*Assistant Examiner*—Timothy Moran
(74) *Attorney, Agent, or Firm*—Browdy and Neimark, P.L.L.C.

(57) ABSTRACT

A scintigraphic device, comprising a collimator, a scintillation crystal structure, a plurality of photomultipliers, electronic circuits for the determination of the position co-ordinates (XY) and energy of the event and their amplification for their subsequent transfer to an electronic processor, wherein photomultipliers ($3_1$, $3_2$, $3_3$, $3_n$) are positioned mutually adjacent, each provided with its own independent electronic circuits ($12_1$, $12_2$, $12_3$, $12_n$), and a circuit (13) for interrogating the respective synchronism signals drawn from the respective electronic circuits (12) determines the signal indicating the photomultiplier (13) that detected the event and enables only a corresponding analogue switch (14) to transfer the signals carrying the position co-ordinates of the event from the enabled electronic components (12) to an analog to digital converter (A/D).

11 Claims, 5 Drawing Sheets

MODULAR HIGH SPATIAL RESOLUTION SCINTIGRAPHIC DEVICE WITH MULTIPLE INDEPENDENT PHOTOMULTIPLIERS AND WITH EXTENSIBLE VISUALISATION AREA

BACKGROUND OF THE INVENTION

The present invention relates to a modular high spatial resolution scintigraphic device with multiple independent photomultipliers and with extensible visualisation area.

In particular, functional imaging systems with small field of view (see U.S. patent applications Ser. Nos. 09/202,894 (now U.S. Pat. No. 6,242,744) and 09/202,790 (now U.S. Pat. No. 6,236,605) in the name of Alessandro Soluri et al.) can be applied in Nuclear Medicine as localisation and diagnostic devices, of reduced weight and minimum size, in order to identify neoplasias with high spatial resolution. Use of said devices can also find application in the scintigraphic analysis of small animals, in order to experiment new radio-marked antibodies, specific for particular pathologies. Another field of application relates to the guided localisation of prostate and breast lesions, in order to identify the areas with higher uptake to be subjected to bioptic sampling, to integrate current radiographic and/or echographic techniques. Such devices can find further applications in Astrophysics and in industrial non destructive test systems.

In particular, the main use of the device relates to locating tumour lesions, especially in those techniques that require an adequate spatial precision such as biopsies (prostate and breast) or in radio-guided or radio-immune-guided surgery. To remove a tumour lesion, the surgeon needs to identify its location and, for this purpose, he/she normally uses the results of diagnostic investigations performed previously with techniques known as RX, CAT scans, NMR and traditional Scintigraphy.

However at the moment of the operation, after "opening" the part, the surgeon may need to locate even more precisely the area to be cut or removed and, for this purpose, he/she can employ a so-called "surgical probe". After injecting into the patient a radio-pharmaceutical, which has the peculiarity of being fixed more specifically in tumour cells, the surgeon uses a probe to detect the gamma-rays emitted by the radioisotope, present in the molecules of the drug in the area examined at a given time. The probe is sensitive to the intensity and energy of the detected gamma radiation and provides analogue signals that are proportional to the radioisotope concentration measured in the region identified by a single channel collimator.

The detected signals are converted to digital form providing information, in a light or sound scale, about the intensity of the signals that fall within the selected energy window. The limitation is constituted by the impossibility of providing an image that describes the spatial map of the concentration of radio-pharmaceutical and that only provides the visualisation of the counts in the area identified by the collimator.

This technique can be replaced with the use of a scintigraphic device which, although its size is fairly reduced, nonetheless still has considerable bulk during the surgical operation. This information has a considerable advantage linked to the real time visualisation of any neoplastic lesions and the confirmation of their total elimination after the surgical removal. Moreover, non scintigraphic techniques exist which allow to locate the sampling areas for needle biopsy, but with limitations on the precision of the areas to sample. These techniques, essentially based on RX and echographic systems, do not use a functional analysis but rather a morphological one, so that biopsies are generally guided in a non specific way.

The limitations of current technologies are mainly due to the poor spatial resolution (about 1 cm) and to the considerable dimensions of current commercial gamma-cameras. Already the devices claimed by Soluri et al. (see U.S. patent applications Ser. Nos. 09/202,894 now U.S. Pat. No. 6,242,744) and 09/202,790), now U.S. Pat. No. 6,232,605) in addition to those claimed by Francesco De Notaristefani et al. (WO 96/37991), Sealock et al. (U.S. Pat. No. 5,783,829), Stan Majewski et al. (U.S. Pat. No. 5,864,141), Scibilia et al. (U.S. Pat. No. 6,021,341), propose improvements both in terms of spatial resolution and in terms of reduced size and weight. Nevertheless, in some applications, the required spatial resolution becomes a fundamental parameter, so it is necessary to improve spatial resolution. Already Soluri et al. have provided an alternative to traditional systems by flat gamma cameras with very limited dimensions. These devices are well suited for specific diagnostic applications, such as, Radio Immune Guided Surgery (RIGS), or Radio Guided Surgery (RGS), or Single Proton Emission Mammography (SPEM), and Positron Emission Mammography (PEM). These applications are only a minimal part of those possible, because single devices can find aplication also in radio guided biopsies, integrating current echographic and/or radiographic technique with scintigraphic ones.

One of the current limitations surely consists of the inability to retrieve the diagnostic information in the dead border zones between individual devices set side by side. In this case if the crystal covers a border area between two photomultipliers, both will see a portion of charge in correspondence with the existing border zone (dead zone). The ambiguity of the event in this case is not easy to forecast and consequently place a limitation to events that fall within the dead zone between neighbouring photomultipliers.

Another fundamental aspect is linked to the limitations imposed by the construction techniques of the Position Sensitive Photomultiplier Tubes (PSPMT). The various models of photomultipliers individually exhibit peripheral dead areas, having total dimensions that exceed the stated active area. This causes problems when photomultipliers set side by side and/or mutually connected are used (see Soluri et al.) in order to obtain flat devices, constituted by multiple individual elements. In these devices it is essential that the dead zone between two bordering photomultipliers be smaller than 8 mm, in such a way as to use the connections of the signals exiting individual photomultipliers to constitute a single sensitive collection area. The presence of photomultipliers dead zones sets an upper limit in coupling devices, with active area that is definitely smaller than the total sizes of the individual photomultipliers.

Therefore, one aim of the invention is to provide a scintigraphic system constituted by the coupling of modules with independent photomultipliers, and in which the Field Of View (FOV) is defined by the way in which the individual modules are spatially positioned, both covering coplanar and contiguous areas, and involving areas of more complex geometry. Reference is also made to a forecasting model (see Raffaele Scafe et al., copyright—software no. 2100001) which allows, in particular, to optimise the components of modular scintigraphic devices (discrete, suitable for panel assembly and individually collimated), based on scintillating crystal arrays, optical guides, PSPMT and electronic balancing networks optimised by the linearity of spatial response in the FOV, in terms of detectability of lesions according to their depth, size and uptake. Essentially, many individual modules can be coupled, each of which has its own dedicated electronics for calculating the detected event position.

Another aim of the invention is to obtain appropriate electronics, to identify unambiguously which photomultiplier was involved by the single event, in order to reconstruct the distribution map of all events observed by the entire device (constituted by the set of individual modules). This independence of the individual modules in calculating the event position over the entire device thus constitutes a substantial innovation relative to the single charge collection surface proposed by Soluri et al. in the past (see U.S. patent applications Ser. Nos. 09/202,894 (now U.S. Pat. No. 6,242,744) and 09/202,790) (now U.S. Pat. No. 6,232,605) in which the individual anode wires belonging to each photomultiplier were connected with the contiguous ones.

A further aim of the invention is to propose an electronic that makes independent the individual detection modules, each with its own individual visualisation area, which uses a single system for digitising and acquiring the signals about single events and which allows an appropriate software to perform the spatial reconstruction of the map of the detected and validated events, starting from the knowledge of the spatial positioning of the individual independent modules.

The subject device can be designed and built using the forecasting model (Raffaele Scafè et al.) that enables to adjust the visualisation area for individual photomultipliers and, in the case of multiple devices, to consider the individual photomultipliers mutually independent, so that the event is attributed unambiguously to the photomultiplier that detected the interaction with the incident radiation.

Yet a further aim of the present invention is that of minimising the dead zones inside the FOV and at its periphery, increasing the active area of the device to coincide with the total photomultiplier area (when a single detection device is used), or the total multiple photomultipliers area (in the case of more complex devices constituted by several photomultipliers and mutually connected in panel assemblies).

SUMMARY OF THE INVENTION

Therefore, the invention, as it is characterised in the claims that follow, solves the problem of providing a modular high spatial resolution scintigraphic device with multiple independent photomultipliers and with extensible visualisation area, comprising in succession from an open end of a container coated with a shielding cladding starting from the source of the event to be detected:

- a collimator made of a material with high effective atomic number, having internally a multiplicity of equal conduits of determined length, identified and separated by septa of a thickness suitable to the energy of the photons to be detected;
- a scintillation crystal structure able to convert the radiation from the source being examined into light radiation;
- a plurality of photomultipliers of the type with crossed anodes or crossed wires receiving the light radiation emitted by the scintillation crystal structure and generating electrical signals proportional to their intensity and identifying the position co-ordinates (XY) of the event;
- electronic circuits to amplify and integrate the signals generated by the photomultiplier to determine the event position co-ordinates and the related energy, according to a resistive chain configuration or to a sum/weighted-sum configuration, for their subsequent transfer to an analog to digital converter and afterwards to a personal computer that processes them and displays on a monitor an image which, from a general point of view, is characterised in that it comprises:
  - a plurality of adjacent photomultipliers, each provided with its own independent electronic circuits for determining the position co-ordinates (X, Y) and the energy of the event detected by the respective photomultiplier, forming detection modules and generating respective synchronism signals;
  - a circuit for interrogating said respective synchronism signals drawn from the respective said electronic components determining the signal indicating the photomultiplier that detected the event;
  - an OR circuit for recognising the signal indicating the photomultiplier that detected the event transmitted by the circuit and enabling only a corresponding analogue switch (14) to transfer the signals carrying the position co-ordinates and the energy of the event from the enabled electronic components to an activated analog to digital converter A/D;
  - a PC-BUS for transferring the digital signals to an electronic processor to be displayed in the form of images by means of a specific software;
  - a system reset circuit that rehabilitates the interrogation and the OR circuits at the conversion completion to make them available and ready to recognise a subsequent event.

BRIEF DESCRIPTION OF THE DRAWING

Further characteristics and advantages of the invention shall become more readily apparent from the description that follows, with reference to the accompanying drawings, provided purely by way of non limiting example, in which the illustrative content of the figures that follows is specified below.

DETAILED DESCRIPTION

Figure 1:
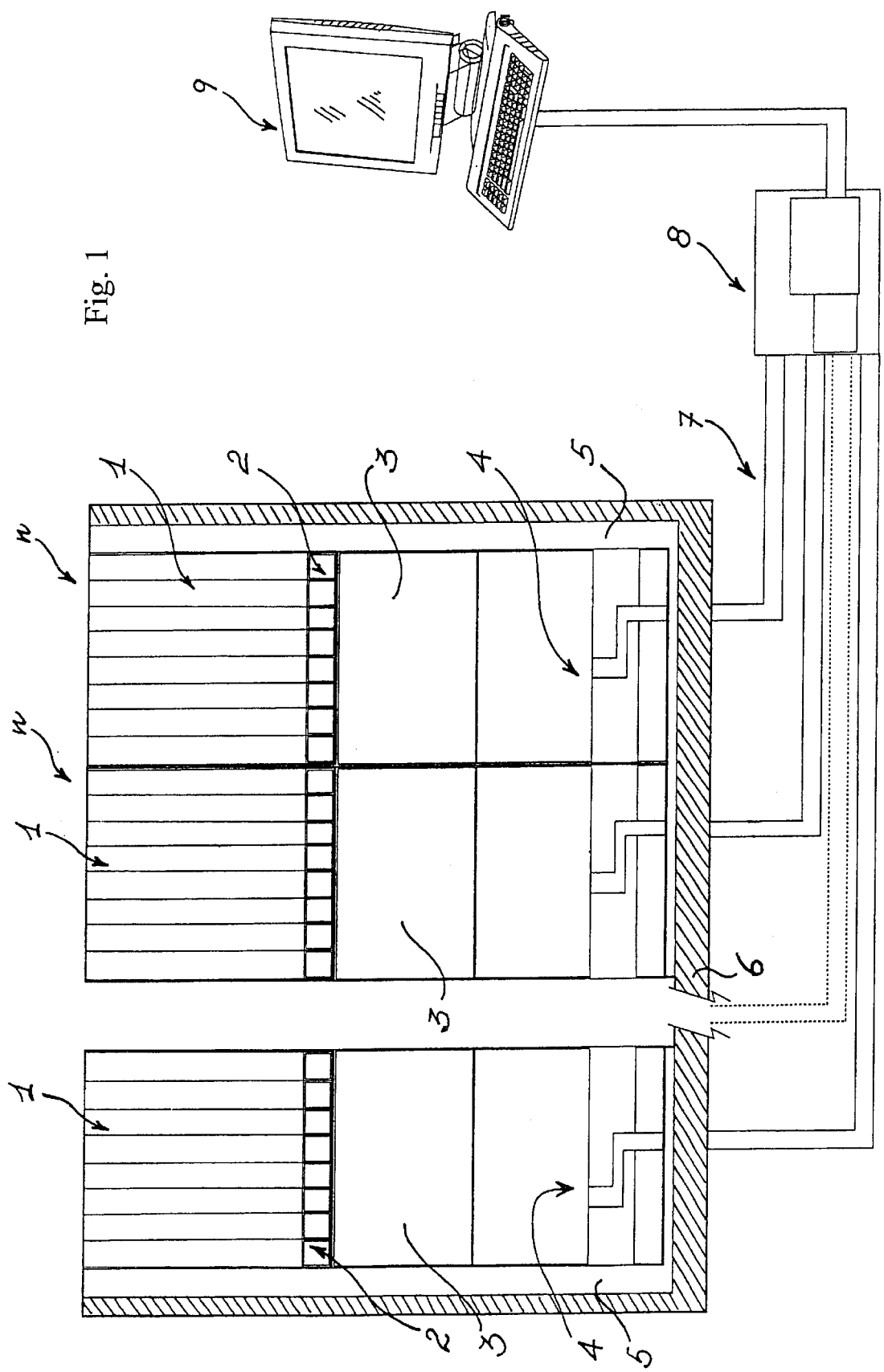
FIG. 1 schematically shows, substantially in blocks, a device according to the invention.

With reference to FIG. 1, a device according to the invention is shown with a multiplicity of independent complexes of collimator and photomultiplier, each defining a detection module n. The collimator may also be a single one. Generically, in FIG. 1 the reference number 1 indicates collimators, 2 scintillation crystal structures, 3 PSPMT photomultipliers, 4 electronic components for conditioning and regulating the charge signals coming from the photomultiplier 3, 5 a container, 6 a shielding cladding, 7 signals and power supply connection cables, 8 a complex of interrogation and discrimination circuits, switches, low voltage power supply and analog-to-digital converters and 9 a personal computer.

Each position sensitive photomultiplier 3 converts the scintillation light signals, corresponding to each single event and emerging from the scintillation crystal structure 2, through a possible coupling optical guide (traditional and of known type, hence not shown herein), in a charge distribution on-the XY plane, thus memorising both the number of light photons generated by the event, and the position of the individual crystal that generated them. This is made possible by an appropriate charge multiplication system, internal to the PSPMT, that amplifies the quantity of charge produced at the photo-cathode in order to allow the operation of the signals conditioning circuits, operating according to known resistive chain or summation/weighted summation configurations, as shall be seen hereafter.

Preferably, the position sensitive photomultiplier to be used is compact, having a total height which can exceed 5 mm. In the case illustrated in FIG. 1 it is a PSPMT 3 of total height for instance equal to 27 mm and provided with a charge collection system with crossed anodes according to the axes X and Y.

In particular the charge collection is performed, inside the PSPMT, by a system with crossed anodes or wires according to the axes X and Y of the plane of the field of view. Alternatively, one can also employ PSPMTs provided with multi-anode systems constituted by individual independent anodes, of polygonal shape and arranged in a matrix. In this case the charge collection can be brought back to the one effected by the PSPMT with crossed anodes, and using the signal conditioning circuits mentioned in the present invention.

Figure 2:
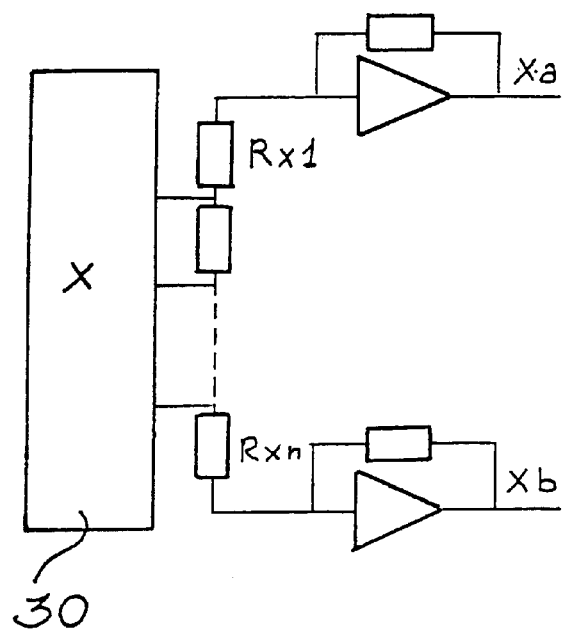
FIG. 2 shows a block diagram of the calibration of the anodic weights in the resistive chain configuration for the device according to the invention.

With reference to FIG. 2, an anodic weight calibration scheme in the resistive network configuration, according to the invention, is shown. In FIG. 2, the number 30 indicates anodes X (the anodes Y are not shown) of a photomultiplier and resistors Rx1, Rxn of predetermined values are positioned immediately downstream of the photomultiplier outputs.

Figure 3:
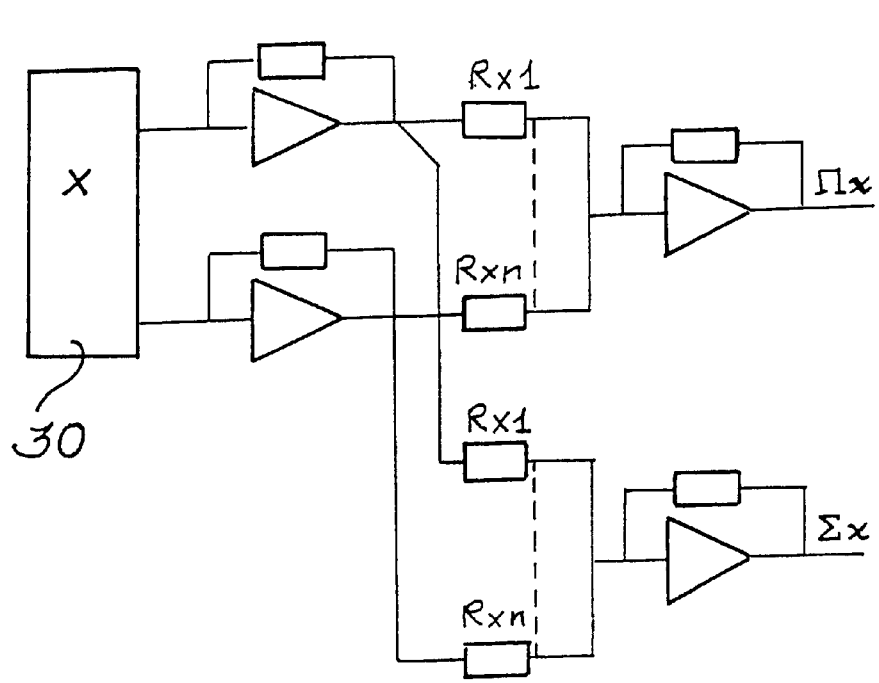
FIG. 3 shows a block diagram of the calibration of the anodic weights in the sum/weighted sum configuration for the device according to the invention.

A similar situation takes place in the case of anodic weight calibration in the sum/weighted sum configuration, as shown in FIG. 3, where the number 30 also indicates anodes X (the anodes Y are not shown) of a photomultiplier and resistors Rx1, Rxn of predetermined values are operatively positioned between the current-voltage conversion operations and the voltage sum operations.

Both proposed schemes, according to the invention, have the task of optimising, through the disposition of the resistors Rx1, Rxn, both for the anodes X and for the anodes Y, the overall spatial response linearity within the field of view of the individual detection module. This calibration can allow, in particular, to obtain a FOV of the individual detection module whose area is equal to the total area of the optical window of the PSPMT, as described below with reference to FIGS. 7 and 8.

In greater detail the introduction of this anodic resistive weights balancing method is based on the determination of the best combination of said weights as a function of the detection module design parameters (crystal pixels transverse dimension, additional optical guide thickness, PSPMT optical window thickness, and anodic configuration of the PSPMT used) that optimises the spatial response linearity over the entire detection module FOV. The balancing is particularly necessary in the peripheral regions of the FOV of the individual detection module, because in them the PSPMT, for geometric and constructive reasons (peripheral dead zones size, number of electrodes in the anodic pack, shape and width of the spatial scintillation light distribution), meets with the greatest sampling difficulties. As for all finite devices, this effect is present, to a different extent, at the edges of the PSPMT.

In order to optimise the characteristics of response linearity over the entire field of view, the charge signals collected at the individual anodes of each photomultiplier constituting the scintigraphic device are weighted, appropriately calibrating the values of the resistors. The calibration values of said resistors Rx . . . are obtained during the bench calibration procedure. This entails that the portion of field of view, controlled by an individual PSPMT, can be dimensioned in such a way as to cover a range of values that vary from even smaller areas than the one reported as active by the manufacturer for the individual photomultiplier, to values which are equal to or greater than the transverse dimensions of the photomultiplier.

On the contrary, the possibility of reducing the FOV of a single scintigraphic device should not be excluded, obtaining in this case a better spatial resolution on a smaller area than the entire surface of the detection module (for instance at his centre). This can be obtained for a single module device dedicated to the analysis of samples which have smaller dimensions than the entire surface of the FOV, when a high spatial resolution is necessary (e.g. analysis on organs of small animals or small fragments of tissue removed for biopsies).

Hence, if one hypothesises that the dead areas of each scintigraphic module have been reduced, each individual device will behave independently, since—as shall be described hereafter according to the invention—appropriate conditioning electronics will handle the signals that identify the detection module involved in the interaction of the event under consideration.

Figure 4:
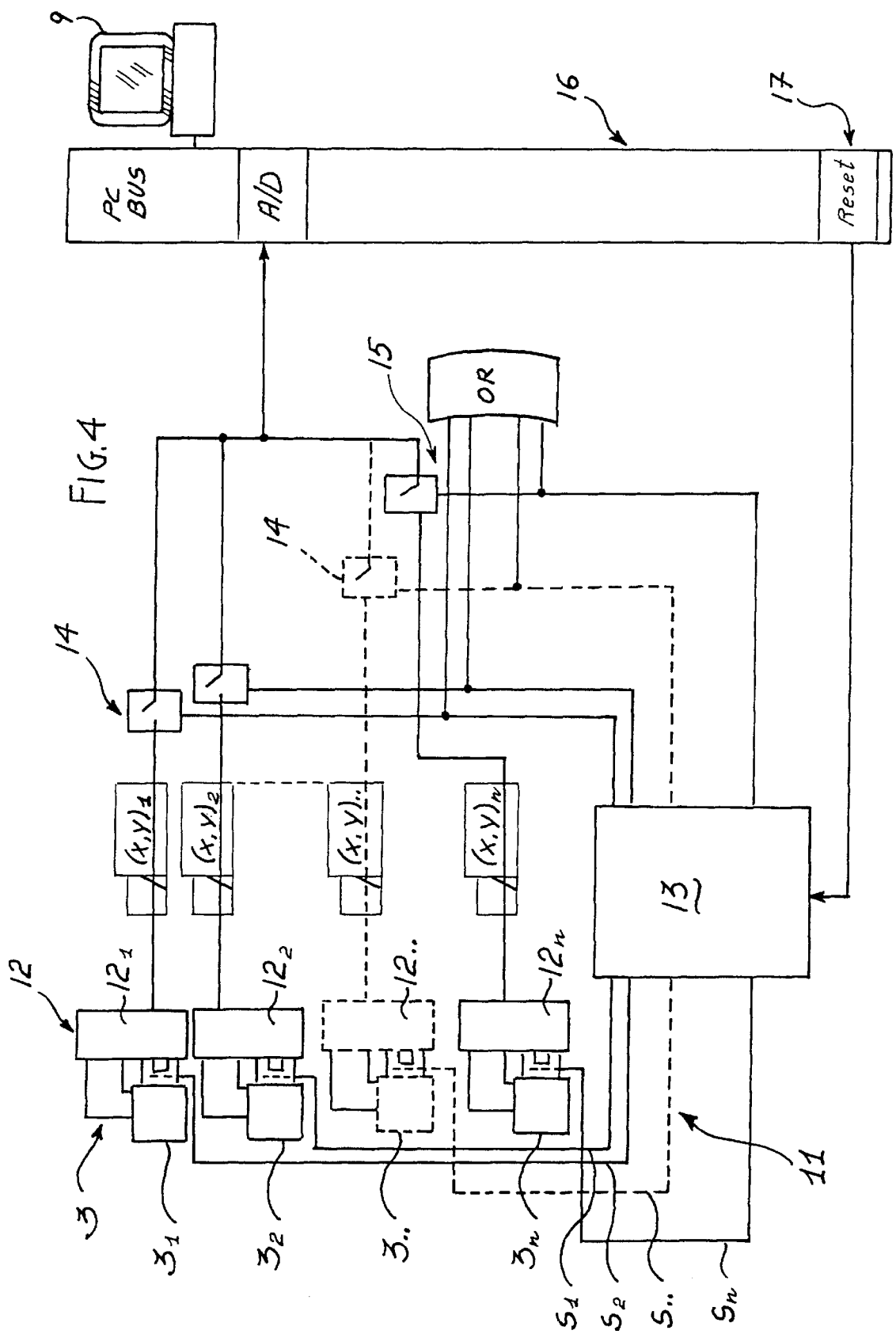
FIG. 4 shows a functional block diagram of the device according to the Invention.

FIG. 4 shows the operating diagram of n detection modules connection in which the number 11 generically indicates synchronism signals transmission lines $S_1, S_2, S_{...}, S_n$ coming, through related electronic circuits $12_1, 12_2, 12_{...}, 12_n$, from a plurality of crossed anodes or wires photomultipliers $3_1, 3_2, 3_{...}, 3_n$ receiving the light radiation emitted by the respective scintillation crystal structures (FIG. 1) and generating electrical signals that are proportional to their intensity and identifying the event position co-ordinates (XY).

The electronic circuits $12_1, 12_2, 12_{...}, 12_n$ perform the amplification and integration of the signals generated by the photomultiplier for determining the event position co-ordinates and the related energy for their subsequent transfer to a personal computer 9 that processes and visualises them on a monitor in the form of an image.

Figure 5:
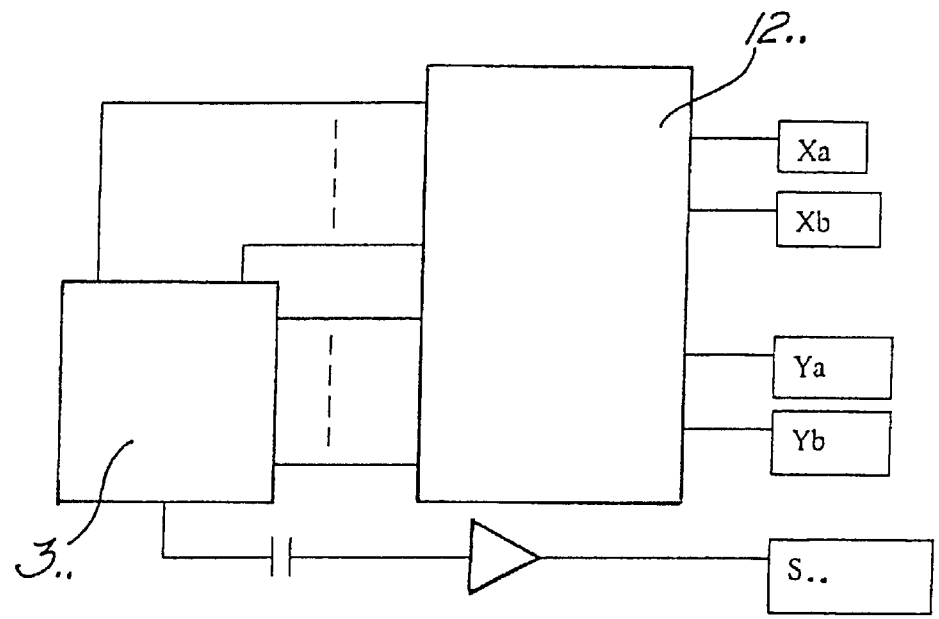
FIG. 5 schematically shows a photomultiplier and related components with a first system for obtaining the synchronism signal.
Figure 6:
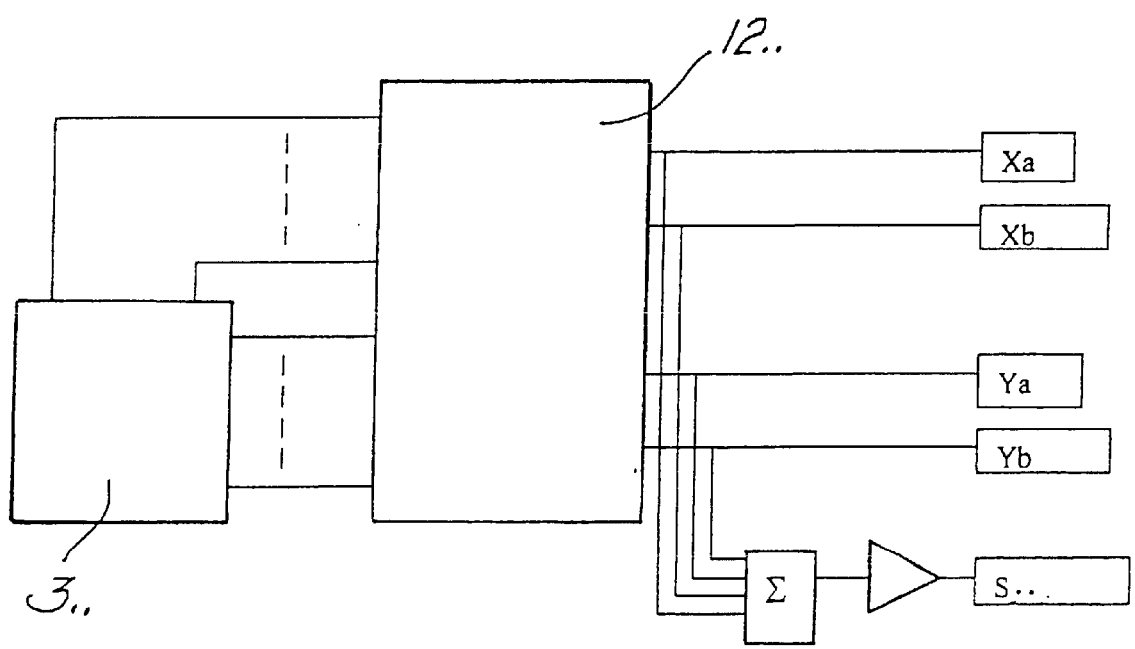
FIG. 6 schematically shows a photomultiplier and related components with a second system for obtaining the synchronism signal.

FIGS. 5 and 6 show two different systems for obtaining the synchronism signal S . . . : the first one uses the amplification of the pulse coming from the last dynode of the photomultiplier 3 . . . , whilst the second one is obtained by analogically summing the signals coming from the anodes, outgoing from the electronic circuits 12 . . .

The diagram in FIG. 4 illustrates the situation in which the charge collected in relation to an individual event involves a single module. The individual synchronism signals of the different detection modules obtained according to said methods of the last dynode or of the sum of the anodic signals will be analysed.

An interrogation circuit 13 collects all synchronism signals S . . . from the lines 11 coming from the electronic circuits 12 . . . associated to each of the n individual modules, considered mutually independent. The function of the circuit 13 is to determine the signal indicating the photomultiplier 3 . . . that detected the event, activating itself at the first incoming signal, amplifying it and remaining insensitive to any other subsequent signals. After the determination of this signal, all are sent to an OR circuit which, having recognised the signal that detected the event as determined by the circuit 13, sends a logic signal 15 that closes a corresponding analogue switch associated to the signals coming from the same detection module that generated it. In this way that switch 14 is closed and the anodic signals useful for computing the position of the event (X, Y)$_1$, (X, Y)$_2$, (X, Y) . . . , (X, Y)$_n$, and of the energy are transmitted towards an analogue-digital converter A/D. The other analogue switches 14, corresponding each to the output of each set of electronic components 12 . . . , remain open, so that from the respective sets of electronic components 12 . . . the transmission of the respective position and energy signals is not enabled.

The diagram of FIG. 4 also illustrates a reset circuit 17 which resets the interrogation circuit 13 and the OR circuit at the end of the analogue-digital conversion operation, making them available and ready to recognise a subsequent even.

In FIG. 4, the reference number 16 indicates a PC-BUS of the system for transferring the digital signals to the personal computer 9 which will thus determine the position of the event on the involved photomultiplier and its energy, visualising them in the form of images by means of a known specific software.

The operating diagram of FIG. 4 illustrates in detail what is generically and schematically shown as 3, 4, 7, 8 and 9 in FIG. 1.

In any case, whether the device is formed by a single detection module or by multiple detection modules and whether the resistive network or sum/weighted sum technique is used, the transduction into analogue form of the charge centroid or of the co-ordinates X, Y of the event is achieved by means of two voltage signals for each co-ordinate corresponding to a total of four signals.

The chain for the signals electronic processing at this point entails the digitisation of said signals by means of analog to digital converters (A/D). The choice of digitising the signals at this processing stage is dictated by purely economic and technological criteria and allows, with the current state of the art, a good compromise between total cost of the system, ergonomics of use, quality of the result obtained and processing speed.

The digitised signals are then transmitted to a personal computer which, by means of a dedicated software, completes the processing chain respectively performing, in the two hypothesised cases: with resistive chain (FIG. 2) and sum/weighted sum (FIG. 3), the following operations for the calculation of the co-ordinates within the detection module FOV involved in the event:

X=Xa/(Xa+Xb), Y=Ya/(Ya+Yb) (not indicated in the figure); in the case of the resistive chain, or:

X=Πx/Σx; Y=Πy/Σy; in the case of sum/weighted sum

The dedicated software is also able to perform further processing operations on the acquired data, able to improve the quality of the final result presented to the user. A fundamental example of further processing is the exclusion of all those events whose energy is higher or lower than predefined threshold, and which therefore do not correspond to events of interest. The energy of the event is easily obtainable, as a sum, from the signals Xa, Xb, Ya, Yb in the case of the resistive chain and from the signals Σx, Σy in the case of the sum/weighted sum. In this way it is possible to eliminate the contribution, in terms of count, of all those events that do not fall within the selected energy window. In other words, they will not contribute to the formation of the image. In this way, it is possible to correct the image comprehensive of the "background", reducing the noise caused by single or multiple interaction in the body tissue. Well set energy thresholds therefore allow to accept only those events that release the energy characteristic of the used tracer within a determined scintillating crystal.

Lastly, a fundamental characteristic of the acquisition/processing system, determined both by the software and by the processor used, is speed. The primary aim of the device is to present to the user, in real time or in near real time, the result of the survey in the form of a graphic image.

A suitable presentation software is able to provide the visualisation of the information as uptake images of the tracers injected into the patient, with the same representation typical of large area scintigraphic devices.

Positioning a scintigraphic device in proximity to the region of interest of the patient's body, into which has been injected a radio-pharmaceutical able to fix itself selectively on the tumour cells and able to emit characteristic radiation of known energy, the surgeon will be able to locate the areas with greater uptake identifying, within the FOV, the areas of different signal (measured radiation intensity) with a spatial resolution of a few mm.

This allows the surgeon to operate with extreme certitude and precision, only in the specific area interested by the tumour, reducing any surgical damages and risks for the patient.

It is also possible to use radio-pharmaceuticals emitting different characteristic energies and hence to offer the possibility of using specific antibodies for determined tumours with different radioisotopes, commonly used in Nuclear Medicine.

In a further variation in accordance with the invention, a PSPMT can be replaced with a similar one having a higher number of dynodes and a higher or lower number of anodes for charge collection. As a consequence, the operating principle described above remains unchanged, and the circuits will be modified to adapt them to the number of photomultiplier anodic outputs.

The dimensions of the PSPMT in use may also vary, reaching active area dimensions that are even larger than those mentioned heretofore, but still such as to be considered miniaturised relative to a traditional, large field of view scintigraphic device, and still such as to allow the achievement of the proposed aims.

In the proposed invention a single PSPMT is used for each detection module n, contrary to scintigraphic devices (large area gamma-cameras) which make use of multiple, non position-sensitive Photomultiplier Tubes (PMT) coupled to a single scintillation crystal to achieve the same aim.

Figure 7:
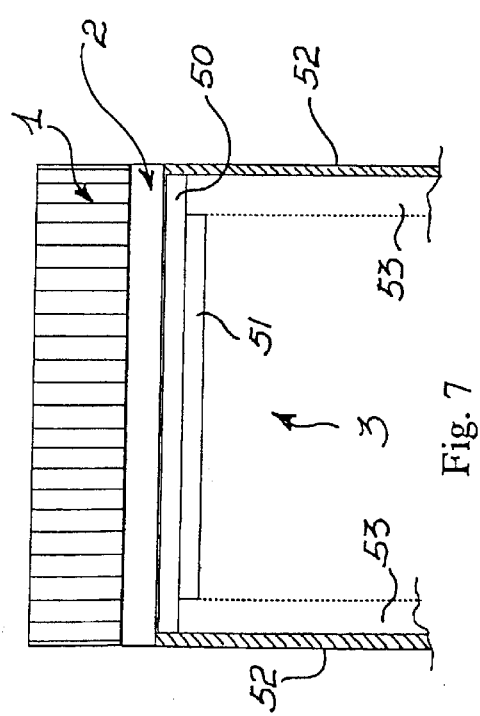
FIG. 7 schematically shows a photomultiplier with collimator and scintillation structure with the related determination of the field of view, according to the invention.

FIG. 7 schematically shows a detection modules assembly that achieve a FOV area greater than the reported area of the photomultiplier in use. The charge weighting values of the resistors Rx . . . (FIGS. 2 and 3) shall be appropriately dimensioned, based on all the constructive parameters of the configurations, to recover the best spatial linearity on the respective FOVs. In FIG. 7, the number 1 indicates a collimator whose width is no less than the widened field of view, 2 a known scintillation crystal matrix whose width is no less than the widened field of view, 50 the field of view, expanded to the maximum extent, of the usefull optical window of the photomultiplier, whose field of view reported by the manufacturer is shown schematically in 51.

Figure 8:
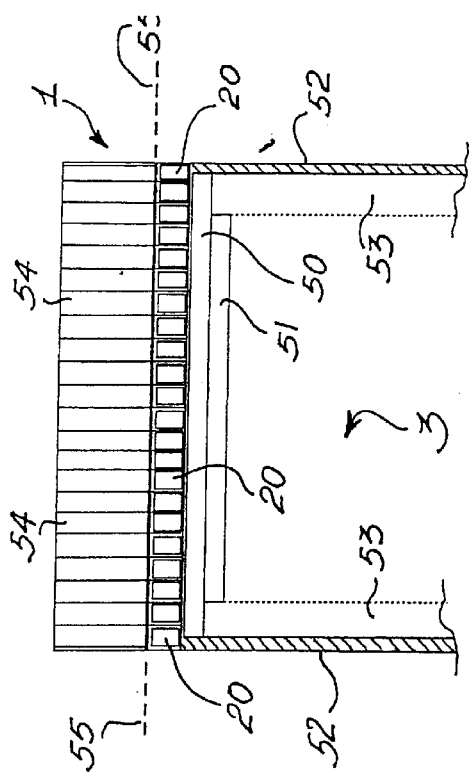
FIG. 8 schematically shows a photomultiplier with collimator and scintillation crystals integrated therein with the related determination of the field of view, according to the invention.

The number 52 indicates the device wall, whilst 53 schematically shows the receiving zone with insufficient or non linear response according to the manufacturer which is recovered through the application of the resistors Rx . . . (FIGS. 2 and 3). FIG. 8 shows a detection module similar to that of FIG. 7, where, instead of the crystal matrix 2 of FIG. 7, the reference number 20 indicates a series of individual crystals, with polygonal section, each completely integrated in respective conforming conduits 54 of the collimator 1 in proximity to its end plane 55. The base faces of the crystals 20 oriented towards the photomultiplier 3 lie on a same plane parallel to said end plane 55 of the collimator.

Figure 9:
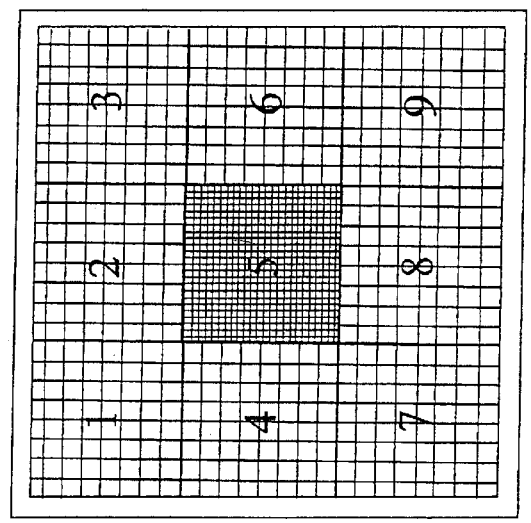
FIG. 9 schematically shows a plan view of a connection of nine detection modules, with different spatial resolution.

FIG. 9 describes an example of application of the device according to the invention in which it is possible to obtain a scintigraphic device constituted by the coupling of nine detection modules based on the electronics described above and using collimators with said integrated crystals 20. In this case for each detection module n distinct collimators are used, where, according to the illustrated example, the pitches of the collimation holes are all equal with the exception of the central module. This module will have a smaller pitch of the collimation hole, i.e. the dimension of the collimator conduit section and of the related integrated crystals, in order to guarantee a better spatial resolution. This design solution allows to obtain a scintigraphic device with differentiated spatial resolution. Its use allows a better quality and flexibility of use of the scintigraphic device because it allows, in addition to real time performance, to dynamically centre on the area with highest spatial resolution of the device (central detection module in FIG. 9) the region of greatest diagnostic interest, measured through the determination of the photomultiplier that detected the event, as described above, to obtain additional diagnostic details.

According to the invention, therefore, each photomultiplier is advantageously provided with its own independent scintillation crystal structure and with its own corresponding independent collimator.

In particular, a combination of scintillation crystal structure and related collimator is differentiated in terms of spatial resolution from the combination of scintillation crystal structure and related collimator of at least one of the adjacent photomultipliers.

The advantages of the present invention pertain to the possibility of obtaining scintigraphic devices that can be optimised according to specific diagnostic applications. The widening of the FOV that can be achieved modifying the electronics through the insertion of the resistors Rx . . . , provides an increment of the field of view obtainable by a single detection module and drastically reduces the effect of the dead zones between the modules set side by side. Moreover, different detection geometries can be obtained because individual independent modules can be suitably assembled, depending on the diagnostic application.

Another advantage, in regard to a single detection module, can be constituted by the ability, on the contrary, to narrow the field of view reported by the photomultiplier, selecting appropriate values for the resistors Rx . . . , to obtain spatial resolution values of less than one millimeter, on a field of view even slightly smaller than the active area reported by the manufacturer for a single PSPMT.

A further advantage linked to the present invention consists of the capability of dividing the field of view also in a non-uniform manner relative to the detection characteristics (for instance spatial resolution, detection efficiency, etc.), by appropriately selecting the dimensions of the collimator holes and of the crystals 20 integrated therein. The advantage consists, for instance, of the ability to have available, during a diagnostic operation, zones of the field of view with differentiated spatial resolution (for instance better at the centre than in the periphery) which can be useful during the procedure (also robotised) for locating a lesion (using the information of the periphery of the field of view) and during the subsequent acquisition of the image (positioning the scintigraphic device in such a way as to centre the lesion in the central area of the field of view).

A further advantage presented by the invention consists of the possibility of assembling a modular scintigraphic device with sections of the overall field of view provided with collimators of different height (but also simultaneously of equal or different collimation pitch). This allows, for instance, to better identify lesions located at different depth, in terms of signal to noise ratio and contrast measured on the obtained image.

Lastly, the invention is susceptible to dedicated applications in various sectors such as Astrophysics, obtaining modules with extended detection areas assembling individual detection modules based on the operating diagram shown in FIG. 4. Industrial applications pertain, for instance, to non destructive testing and diagnosing systems that can be obtained with devices that employ the proposed techniques.

Obviously, moreover, the constructive details and the embodiments can vary widely from those described and illustrated herein purely by way of example, without thereby departing from the scope of the present invention as claimed hereafter.

What is claimed is:

1. A modular high spatial resolution scintigraphic device with multiple independent photomultipliers and with extensible visualisation area, comprising in succession from an open end of a container coated with a shielding cladding starting from the source of the event to be measured:

at least a collimator (1) made of a material with high atomic number, internally having a multiplicity of equal conduits of determined length, identified and separated by septa of thickness suited to the photons energy to be detected;

a scintillation crystal structure (2; 20) able to convert the radiation from the source under examination into light radiation;

a plurality of crossed anodes or wires photomultipliers (3 . . . ) receiving the light radiation emitted by the scintillation crystal structure and generating electrical signals proportional to their intensity and identifying the single event position co-ordinates (XY);

electronic circuits (12 . . . ) able to execute the amplification and integration of the signals generated by the photomultiplier for the determination of the event position co-ordinates (XY) and the related energy, according to a resistive chain configuration or according to a sum/weighted sum configuration, for their subsequent transfer to a conversion device and thence to a personal computer that processes them and visualises them on a monitor in the form of an image, characterised in that it comprises:

a plurality of photomultipliers ($3_1$, $3_2$, $3_3$, $3_n$), positioned mutually adjacent, each provided with its own independent electronic circuits ($12_1$, $12_2$, $12_3$, $12_n$), for determining the position co-ordinates (X, Y) and the energy of the event detected by the respective photomultiplier, forming detection modules and generating respective synchronism signals ($S_1$, $S_2$, $S_{...}$, $S_n$);

a circuit (13) for interrogating said respective synchronism signals drawn from the respective said electronic circuits (12 . . . ) determining the signal indicating the photomultiplier (3 . . . ) that detected the event;

an OR circuit for recognising the signal indicating the photomultiplier (3 . . . ) that detected the event transmitted by the circuit (13) and enabling only a corresponding analogue switch (14) to transfer the signals carrying the position co-ordinates and the energy of the event from the enabled electronic components (12 . . . ) to an activated analog to digital converter (A/D);

a PC-BUS (16) for transferring the digital signals to a personal computer (9) to be displayed in the form of images by means of a specific software;

a system reset circuit (17) that resets both the interrogation circuit (13) and the (OR) circuit at the completion of the conversion operation to make them available and ready to recognise a subsequent event.

2. A scintigraphic device as claimed in claim 1, characterised in that said synchronism signals ($S_1$, $S_2$, $S_{...}$, $S_n$) are obtained from the individual sets of electronic components of the photomultipliers drawing and amplifying the signal coming from the last dynode of each photomultiplier.

3. A scintigraphic device as claimed in claim 1, characterised in that said synchronism signals ($S_1$, $S_2$, $S_{...}$, $S_n$) are obtained from the individual sets of electronic components of the photomultipliers by analogue sum of the signals coming from the anodes.

4. A scintigraphic device as claimed in claim 1, characterised in that the independent electronic components of each photomultiplier comprises resistors (Rx1, Rx2, Rx . . . , Rxn) of predetermined value to optimise the response linearity characteristics over the entire field of view of each detection module.

5. A scintigraphic device as claimed in claim 4, wherein the electronic components perform the amplification and integration of the signals generated by the photomultiplier for the determination of the position co-ordinates (XY) of the event and the related energy according to a resistive chain configuration, characterised in that the independent electronic components (12 . . . ) of each photomultiplier (3 . . . ) comprises resistors (Rx1, Rx2, Rx . . . , Rxn) positioned immediately downstream of the outputs of the photomultipliers (3 . . . ).

6. A scintigraphic device as claimed in claim 4, wherein the electronic components perform the amplification and integration of the signals generated by the photomultiplier for the determination of the position co-ordinates (XY) of the event and the related energy according to a sum/weighted sum configuration, characterised in that the independent electronic circuits (12 . . . ) of each photomultiplier (3 . . . ) comprises resistors (Rx1, Rx2, Rx . . . , Rxn) operatively positioned between the operations of current-voltage conversion and the operations of voltage summation.

7. A scintigraphic device as claimed in claim 1, characterised in that each photomultiplier (3 . . . ) is provided with its own independent scintillation crystal structure (2, 20) and with its own corresponding independent collimator (1).

8. A scintigraphic device as claimed in claim 7, characterised in that the scintillation crystal structure (20) is constituted by a multiplicity of individual crystals with polygonal section, each completely integrated in proximity to the extremity, oriented towards the photomultiplier, of each collimator conduit (1), having conforming polygonal section, with all the base faces of the crystals oriented towards the photomultiplier lying in a common plane parallel to an end plane of the collimator.

9. A scintigraphic device as claimed in claim 7, characterised in that the scintillation crystal structure (2, 20) and the related collimator (1) of said adjacent photomultipliers (3 . . . ) are different from at least one of the adjacent crystal structures and collimators.

10. A scintigraphic device as claimed in claim 9, characterised in that a combination of scintillation crystal structure (2, 20) and of related collimator (1) is differentiated in spatial resolution and detection efficiency from the combination of scintillation crystal structure and related collimator of at least one of the adjacent photomultipliers (3).

11. A scintigraphic device as claimed in claim 1, characterised in that the independent electronic components (12 . . . ) of each photomultiplier (3 . . . ) comprise resistors (Rx . . . ) to optimise the characteristics of response linearity over the entire field of view, and the scintillation crystal structure (2; 20) and related collimator (1) extend in width beyond the active detection surface reported by the manufacturer of the photomultiplier until covering the entire optical window of the photomultiplier.

* * * * *